US005763693A

United States Patent [19]

Hirata et al.

[11] Patent Number: 5,763,693
[45] Date of Patent: Jun. 9, 1998

[54] PROCESS FOR PRODUCING ISOPROPYL ALCOHOL

[75] Inventors: Shigeru Hirata; Shinji Ogawa, both of Yokohama, Japan

[73] Assignee: Mitsui Chemicals, Inc., Tokyo, Japan

[21] Appl. No.: 604,622

[22] Filed: Feb. 21, 1996

[51] Int. Cl.$^6$ .................................................. C07C 29/04
[52] U.S. Cl. ............................................... 568/895
[58] Field of Search .............................................. 568/895

[56] References Cited

U.S. PATENT DOCUMENTS

| 4,469,903 | 9/1984 | Schmidt . | |
|---|---|---|---|
| 5,268,515 | 12/1993 | Irvine | 568/895 |

FOREIGN PATENT DOCUMENTS

| 0354243 | 2/1990 | European Pat. Off. . |
| 45-33165 | 10/1970 | Japan . |
| 60-24082 | 6/1985 | Japan . |
| 61-100181 | 5/1986 | Japan . |
| 62-25982 | 2/1987 | Japan . |
| 62-25983 | 2/1987 | Japan . |
| 62-25984 | 2/1987 | Japan . |
| 62-29988 | 2/1987 | Japan . |
| 2-24257 | 5/1990 | Japan . |
| 3-29393 | 4/1991 | Japan . |
| 5-36418 | 5/1993 | Japan . |
| 5-36419 | 5/1993 | Japan . |
| 1208144 | 10/1970 | United Kingdom . |
| 1517334 | 7/1978 | United Kingdom . |

OTHER PUBLICATIONS

Patent Abstracts of Japan, vol. 011, No. 202, (C–432), Jun. 30, 1987 & JP 62025982A, Feb. 1987 *Abstract*.
Patent Abstracts of Japan, vol. 011, No. 202, (C–432), Jun. 30, 1987 & JP 62025983A, Feb. 1987 *Abstract*.
Patent Abstracts of Japan, vol. 015, No. 150, (C–0824), Apr. 16, 1991 & JP 03027336A, Feb. 1991 *Abstract*.

*Primary Examiner*—Alan L. Rotman
*Assistant Examiner*—Jean F. Vollano
*Attorney, Agent, or Firm*—Burns, Doane, Swecker & Mathis, L.L.P.

[57] ABSTRACT

In a process for producing isopropyl alcohol by direct liquid phase hydration of propylene and water in the presence of a strong acid solid catalyst at a high temperature and a high pressure, the reaction is carried out at a temperature in a ranging between 100° and 250° C. and a pressure in a ranging between 60 and 200 atm in an excess of water. Then, a liquid phase of the reaction product is contacted with an extraction agent of a saturated hydrocarbon having 3 or 4 carbon atoms at a temperature in a ranging between the critical temperature of the extraction agent and the temperature higher than the critical temperature by 40° C. under a pressure ranging between the critical pressure of the extraction agent and 200 atm at an S/F ratio ranging between 0.3 and 3 which is calculated from the equation of the amount of the extraction agent divided by the amount of the extract feed. Finally, after isopropyl alcohol is extracted from the liquid phase, it is separated from the resultant extract phase thus obtained. According to this process, the energy required for concentrating isopropyl alcohol is reduced, and also large-scale production facilities are not necessary.

26 Claims, 2 Drawing Sheets

PROCESS FOR PRODUCING ISOPROPYL ALCOHOL

BACKGROUND OF THE INVENTION

1. Field of the Invention

This invention relates to a process for producing isopropyl alcohol, which is industrially used as paint solvents, medical and pharmaceutical supplies, agricultural chemicals, synthetic raw materials, and cleaning agents, by means of liquid phase direct hydration of propylene.

2. Description of the Related Art

Production of isopropyl alcohol by the liquid phase direct hydration of propylene is well known in the art as well as production of sec-butyl alcohol by hydration of butene. The hydration requires an acid catalyst. An available process for industrial production of alcohol uses a strong acid cation exchange resin or a heteropolyacid catalyst.

For example, there is a process for producing alcohol using a solid catalyst such as a strong acid cation exchange resin, in which the hydration is carried out at a temperature of between 100° and 150° C. and a pressure of between 60 and 200 atm. On the contrary, a typical process using the heteropolyacid catalyst is carried out at a temperature of between 150° and 250° C. and a pressure of between 100 and 200 atm. As apparent from the above, the former process requires the lower temperature and the lower pressure and is thus superior to the latter one in view of the construction of a reactor.

As well known in the art, the raw material propylene can be converted at a high conversion rate of at least 75% by selecting the reaction conditions adequately (Japanese Patent Publication No. SHO 45-33165) in the process of liquid phase direct hydration of propylene using a solid catalyst. However, a high selectivity of from 95 to 99% of isopropyl alcohol can only be achieved by controlling by-production of isopropyl ether during the reaction. For this purpose, typical processes require at least ten times in mole as much water as that of the raw material propylene to be supplied into an inlet of the reactor. As a result, almost all of the liquid phase is water at an outlet of the reactor and the resultant aqueous solution of crude isopropyl alcohol has a concentration of as low as 10–30% by weight.

On the other hand, most isopropyl alcohol used industrially is anhydrous, and therefore it is required to concentrate the crude isopropyl alcohol solution of a low concentration thus obtained to be anhydrous. Generally, isopropyl alcohol forms an azeotropic mixture with water which contains 88% by weight of isopropyl alcohol. Therefore, in the industrial field, the crude isopropyl alcohol is typically concentrated to the concentration of the azeotropic composition by means of distillation, and is then dehydrated by means of azeotropic distillation using an adequate entrainer such as benzene, and is finally manufactured as an anhydrous product by fractionation. The energy required for the concentration is thus tremendously large.

For reducing such energy necessary for concentrating alcohol, some processes have been proposed. According to Japanese Patent Publication No. HEI 2-24257, in producing sec-butyl alcohol from n-butene and water using a liquid phase heteropolyacid as a catalyst, liquid phase hydration is carried out at a temperature higher than the critical temperature of n-butene under a pressure higher than the critical pressure thereof. Next, a gaseous phase of the reaction mixture mainly consisting of unreacted n-butene is continuously drawn out of a reactor and is liquefied by cooling. Then, the liquefied phase is separated into a light liquid phase mainly consisting of the unreacted n-butene and sec-butyl alcohol produced by the reaction, and a heavy liquid phase mainly consisting of water. Finally, almost anhydrous sec-butyl alcohol can be obtained by distilling the light liquid phase to remove the unreacted n-butene.

This process does not require the stage for dehydrating the crude alcohol, and thus in appearance said process is a preferable example in which the energy for the concentration is largely reduced. However, since the conversion of the raw material butene in the reactor is only about 10%, there is an industrial problem that it is required to re-compress and recycle the unreacted butene in the amount of more than nine times in mole as much as the stoichiometric amount necessary for producing alcohol as well as the problem that the volume of the reactor becomes large.

Japanese Patent Publication No. SHO 60-24082 describes a process for producing lower alcohol having 2–6 carbon atoms by means of direct catalytic hydration of gaseous lower olefin having 2–6 carbon atoms with liquid water in the presence of a strong acid solid substance at a high temperature and a high pressure and then separating crude alcohol from the reacted mixture. This process is characterized by: (1) introducing a vapor stream containing olefin into the bottom of a reactor which is filled with an acid catalyst, and charging at least 1 mole of liquid water per 1 mole of olefin to be reacted into the reactor; (2) reacting the vapor stream and the liquid water at a temperature higher than or at least slightly lower than the critical temperature of olefin under a pressure higher than or at least slightly lower than the critical pressure of olefin; (3) leaving all of the liquid phase of the reacted mixture in the reactor or returning the major part of the water phase to the reactor; (4) discharging the vapor stream containing the unreacted olefin and almost all of the substance produced by the reaction from the top of the reactor; and (5) separating the crude product mainly consisting of the produced alcohol in the form of liquid from the discharged vapor stream.

According to this process, the selectivity of isopropyl alcohol in the reaction is high, and isopropyl alcohol to be separated in the form of liquid is highly concentrated. Furthermore, such a high selectivity is considered to relate to the fact that the concentration of the isopropyl alcohol is kept extremely low in the liquid phase since the reaction product produced by the reaction transfers to the gaseous phase directly. According to the example of the publication, the selectivity of isopropyl alcohol is 99% or higher and 80% by weight of the separated liquid substance is isopropyl alcohol, when the liquid phase hydration is carried out at 135° C. and 100 atm. In this example, even though the resultant isopropyl alcohol is highly concentrated, it does not reach the concentration of 88% by weight of the azeotropic composition. Furthermore, 4.2 moles of isopropyl alcohol is obtained per hour to provide the overall reaction conversion of 75%, when 5.6 moles of newly charged propylene is supplied per hour. However, it is obvious that the reaction conversion per one path from the inlet to the outlet of the reactor is lower than 75%, though no clear description is made, since a part of the vapor drawn out of the outlet of the reactor is recycled into the inlet of the reactor.

According to the findings of the inventors of the present invention, in order to carry out the hydration keeping the isopropyl alcohol in the liquid phase, an extremely low concentration at 135° C. and 100 atm as in the process described in the publication, a large volume of gaseous phase of the reacted mixture is required to be recycled into the reactor. For example, it has been found that the conversion of propylene from the inlet to the outlet of the reactor is as low as about 8%, when the reaction is carried out such that the concentration of the isopropyl alcohol in the liquid phase is 10% by weight or lower. Therefore, in the process of the publication, the reaction conversion of the raw material olefin is low, the volume of the reactor becomes large, and a large amount of unreacted olefin is required to be recycled, as in the process of above-mentioned Publication No. HEI 2-24257. Thus, the process described herein is not a direct solution to the problem currently existing in the industrial field.

More specifically, in this process in which the alcohol synthesized by the liquid phase hydration of olefin is collected at a high concentration from the gaseous phase of the reacted mixture, the alcohol synthesized in the liquid phase existing in the reactor is, in appearance, extracted by means of the unreacted raw material olefin also existing in the reactor. Thus, it is reasonable that the conversion of the raw material olefin is low, and it is inevitable that the volume of the reactor and the amount of the unreacted olefin to be recycled becomes large.

On the other hand, a process is proposed which is for more effectively concentrating the low concentration crude alcohol aqueous solution obtained by hydration of olefin or fermentation. In the process, alcohol contained in the liquid phase is highly concentrated by performing an extraction using $CO_2$ or hydrocarbons group as an extraction agent in the conditions in which the extraction agent becomes super-critical fluid, sub-critical fluid or liquid.

The "sub-critical fluid" herein means the state of a substance as an extraction agent being at a temperature near the critical temperature of the substance under a pressure near the critical pressure thereof. More specifically, the sub-critical fluid is the state of the substance where one of the temperature and the pressure is higher than the critical value of the substance and the other is a little lower than the critical value, or both of the temperature and the pressure are a little lower than the critical value.

Japanese Patent Laid-open No. SHO 62-25982 discloses a process for concentrating and purifying alcohol, which is characterized by comprising the following steps of: adding an extraction agent to a mixture consisting of fermented alcohol, organic liquid consisting of impurities having a high boiling point, and water; contacting and mixing the mixture with the extraction agent in the condition in which the extraction agent becomes a super-critical or sub-critical state; introducing the mixture into an extraction-separation tank to separate it into the raffinate phase containing water as a main component, the major part of the impurities having a high boiling point, a part of the alcohol and the extraction agent, and the extract phase containing the extraction agent as a main component, the major part of the alcohol and a part of the impurities having a high boiling point; transferring the extract phase from the extraction-separation tank to the impurity-separation tank; and reducing the pressure of the impurity separation tank. By this process, highly concentrated alcohol containing substantially no impurity having a high boiling point can be collected.

According to the example shown in this laid-open application, $CO_2$ of an extraction agent is mixed with 10% by weight of ethanol aqueous solution in the amount of six times in weight as much as that of the ethanol aqueous solution (an S/F ratio of 6, S: the amount of the extraction agent, F: the amount of the extraction feed). Next, the mixture is contacted at 40° C. and 110 atm, and is separated into the extract phase and the raffinate phase in the extraction-separation tank. Then, the extract phase is transferred from the tank to an impurity-separation tank. Finally, the impurities are separated by reducing pressure to 80 atm while maintaining the temperature constant. As a result, the composition free of $CO_2$ of the residue in the impurity-separation tank are approximately 80% by weight of ethanol and 20% by weight of water.

For practically utilizing the process for concentrating alcohol described in the above laid-open application, it is essential to collect substantially all of $CO_2$ of the extraction agent used in the large amount of sixty times in weight as much as that of alcohol, and to recycle such $CO_2$. According to the findings of the inventors of the present invention, in order to separate highly concentrated alcohol containing no $CO_2$ from the residue in the impurity-separation tank mainly consisting of $CO_2$ by chiefly reducing the pressure as in a known process, it is necessary to reduce the pressure of the residue in the impurity-separation tank further to a pressure in the range between the atmospheric pressure and several atm since $CO_2$ is easily dissolved into alcohol. The process in the laid-open application is directed to concentrated fermented alcohol, i.e., ethyl alcohol, and the same problem occurs when isopropyl alcohol is concentrated by the same process as in the laid-open application. Therefore, the energy necessary for re-compressing and recycling $CO_2$ of the extraction agent collected after the separation of a high-concentrated alcohol aqueous solution under such a low pressure is extremely large to cause a significant problem in utilizing the process practically.

Japanese Patent Laid-open Nos. SHO 62-25983, 62-25984 and 62-29988 propose a process for enhancing the efficiency in extracting alcohol using $CO_2$ as an extraction agent and for separating more completely into an extract phase and a raffinate phase, and also for separating the extract phase into the extraction agent and the solute (highly concentrated alcohol) by means of a multi-stage extraction and a multi-stage reduction of pressure. However, the separation has not been attained enough in this process, and there is still a problem concerning the large power for re-compressing and recycling the extraction agent as well as the necessity for a large-scale equipment. Thus, many problems have to be solved before utilizing the process practically.

Japanese Patent Laid-open No. SHO 61-100181 discloses a process comprising the following steps of: separating crude alcohol from an extract phase obtained by contacting a low-concentrated alcohol aqueous solution and $CO_2$ of an extraction agent by reducing the pressure of said extract phase; supplying the resultant crude alcohol to an azeotropic distillation tower using benzene as an entrainer to dehydrate the crude alcohol therein while collecting $CO_2$ dissolved in the crude alcohol from a partial condenser equipped at the top of the tower to re-compress and recycle the collected $CO_2$ of the extraction agent. The process described in the laid-open application gives a certain solution for completely separating and collecting $CO_2$ of the extraction agent dissolved in the crude alcohol. However, since the amount of $CO_2$ of the extraction agent to be recycled is still large, the substantial problems concerning the large power for compressing and recycling the extraction agent and the large size of the equipment for extraction have not been solved by this process.

Japanese Patent Publication No. HEI 5-36418 discloses a process comprising the steps of: supplying an extraction feed mainly consisting of alcohol and water to the top of a countercurrent extraction tower, and an extraction agent selected from the group of propane, propylene, n-butane and i-butane to the bottom of the tower; contacting the feed and the extraction agent countercurrently in the conditions in which the extraction agent is in a super-critical or sub-critical state in the countercurrent extraction tower; drawing out an extract phase containing concentrated alcohol from the top of the extraction tower; liquefying the extract phase by cooling to separate the extract phase into two phases; refluxing all of a heavy liquid phase containing a lot of water to the top of the extraction tower, and introducing a light liquid containing a lot of hydrocarbon into a distillation tower; separating the hydrocarbon and alcohol by distillation; and finally obtaining almost anhydrous alcohol from the bottom of the distillation tower. According to this process, the energy necessary for concentrating alcohol is only approximately from one third to one fifth of that in a known distillation, since the heat released during the re-compression of the hydrocarbon of the extraction agent recovered from the top of the distillation tower can be effectively used in a reboiler of the tower.

However, in this process, the anhydrous alcohol collected from the bottom of the distillation tower contains the hydrocarbon of the extraction agent in the amount of 1.5 times in weight as much as that of the alcohol, as apparent from the description and the material balance of the above publication, so that it is necessary to collect (by distillation) the hydrocarbon from the anhydrous alcohol and to re-compress and recycle the hydrocarbon as the extraction agent for utilizing the process practically. Furthermore, though 10% by weight of alcohol can be concentrated to almost anhydrous (approximately 99.9% by weight), still remains such a problem as the large power for re-compressing and recycling the hydrocarbon of the extraction agent and the large-scale extraction equipment are required since the S/F ratio is as large as 5 or larger.

Japanese Patent Publication No. HEI 3-29393 discloses a process for collecting almost anhydrous highly concentrated alcohol by the following steps: supplying an alcohol aqueous solution as an extraction feed to the middle of a countercurrent extraction tower, and supplying propane of an extraction agent to the bottom of the extraction tower to extract alcohol; setting the condition of the propane such that it becomes super-critical or sub-critical at the portion lower than an inlet of the extraction feed, and that it becomes liquid at the portion higher than the same inlet; drawing out an extract phase in the form of liquid mainly consisting of the propane from the top of the extraction tower; and distilling the extract phase.

According to the example of this publication, 10% by weight of alcohol aqueous solution of the extraction feed can be concentrated to about 95–98% by weight (propane-free) of alcohol by adequately setting the extraction conditions. However, the S/F ratio is still as large as 3 or larger, and the problems concerning the power for re-compressing and recycling the extraction agent and the size of the extraction facilities are not fully solved.

Japanese Patent Publication No. HEI 5-36419 proposes a process for extracting alcohol using $CO_2$ as an extraction agent based on the same principle as that of the process in Publication No. HEI 3-29393. Since the necessary S/F ratio is as large as 10 or larger in the process in No. HEI 5-36419, this process is practically inferior to the process in No. HEI 3-29393 which utilizes hydrocarbon (propane) as the extraction agent. Thus, the process in No. HEI 5-36419 does not substantially solve the problems.

As mentioned above, in the process for extracting alcohol using the extraction agent being in the super-critical or sub-critical state, a large compressing power is required to recycle the extraction agent, and also it is difficult to collect the extraction agent after the extraction since the extraction agent exists in the form of gas at the ambient temperature and the atmosphere pressure. Furthermore, such a process requires large-scale facilities since all of the extraction tower and its accessory equipment should be high pressure facilities. For these points, this process is substantially different from a liquid-liquid extraction process which has been widely employed in the industrial field. For example, with regard to the power for compressing and recycling the extraction agent, the necessary power per unit weight of the extraction agent in the extraction process is incomparably larger than in the liquid-liquid extraction process. Thus, even if alcohol can be concentrated to be substantially anhydrous without using the conventional dehydration process by means of distillation, such large power is required for compressing and recycling the extraction agent that the process is often rather disadvantageous in view of the energy consumption. Therefore, in putting such extraction process into practice, it is important to considerably reduce the S/F ratio in the extraction, that is, the amount of extraction agent to be recycled, rather than to extract alcohol so as to be concentrated as highly as possible in order to attain the object of reducing the energy required for concentrating alcohol.

SUMMARY OF THE INVENTION

An object of the present invention is to provide a process for producing isopropyl alcohol which, in producing isopropyl alcohol by means of liquid phase direct hydration of propylene, requires a reduced energy consumption for concentrating the isopropyl alcohol and also does not need large-scale production facilities by continuously carrying out under preferable conditions the liquid phase hydration of propylene with a high conversion of propylene in the reaction, and also extraction of isopropyl alcohol from a liquid phase of the reacted mixture to efficiently obtain crude isopropyl alcohol aqueous solution at an adequate concentration.

The present invention relates to a process for producing isopropyl alcohol by direct hydration of propylene and water at a high temperature and a high pressure in the presence of a strong acid solid catalyst, and separation of crude isopropyl alcohol aqueous solution from the resultant reacted mixture followed by purifying the solution. More specifically, the process comprises the steps of:

(1) feeding continuously propylene and water in the amount of at least 1 mole per 1 mole of propylene to be reacted into a reactor in which a solid catalyst is packed or suspended to react them at a temperature in a range between 100° and 250° C. and a pressure in a range between 60 and 200 atm;

(2) drawing out continuously the total amount of a gaseous phase and a liquid phase of the reacted mixture from the reactor;

(3) feeding the gaseous phase of the reacted mixture to a distillation tower to remove impurities mainly consisting of propane contained in the raw material propylene from the bottom of the tower and to collect unreacted propylene from the top of the tower so as to recycle the unreacted propylene into an inlet of the reactor;

(4) contacting the liquid phase of the reacted mixture with an extraction agent of a saturated hydrocarbon having 3 or 4 carbon atoms at a temperature ranging between the critical temperature of the extraction agent and the temperature higher than the critical temperature by 40° C. under a pressure in a range between the critical pressure of the extraction agent and 200 atm at the S/F ratio ranging between 0.3 and 3, and extracting isopropyl alcohol produced by the reaction from the liquid phase of the reacted mixture;

(5) recycling the major amount of the raffinate mainly consisting of water; and (6) separating the isopropyl alcohol as a highly concentrated aqueous solution from the extract phase mainly consisting of the saturated hydrocarbon, and purifying the solution to obtain purified isopropyl alcohol.

2. The process comprises the step of separating the extract phase into the gaseous phase mainly consisting of the saturated hydrocarbon and the liquid phase mainly consisting of isopropyl alcohol and water by reducing the pressure of the extract phase to the critical pressure of the saturated hydrocarbon or lower to obtain the isopropyl alcohol produced by the reaction as the highly concentrated aqueous solution from the extract phase, which is obtained by contacting the liquid phase of the reacted mixture and the extraction agent and mainly consists of the saturated hydrocarbon, or 3. the process comprises the step of separating the extract phase into a light liquid phase mainly consisting of the saturated hydrocarbon and a heavy liquid phase mainly consisting of isopropyl alcohol and water by cooling the extract phase to the critical temperature of the saturated hydrocarbon or lower while substantially maintaining the pressure of the extract phase to obtain the isopropyl alcohol produced by the reaction as highly concentrated solution from the extract phase.

4. The process further comprises the step of recycling as the extraction agent the major amount of the saturated hydrocarbon remaining after the separation of the isopropyl alcohol produced by the reaction as highly concentrated aqueous solution from the extract phase mainly consisting of the saturated hydrocarbon, which is obtained by contacting the liquid phase of the reacted mixture and the extraction agent.

5. The process further comprises the steps of drawing out a part of the saturated hydrocarbon to be recycled as the extraction agent, and feeding the saturated hydrocarbon to the distillation tower together with the gaseous phase of the reacted mixture to separate the saturated hydrocarbon from the bottom of the distillation tower.

6. And in the process, the saturated hydrocarbon is preferably propane.

7. In the process, there is used propane that is contained in the raw material propylene and that is separated from the bottom of the distillation tower at the stage of collecting the unreacted propylene by distillation.

BRIEF DESCRIPTION OF THE DRAWINGS

In FIG. 1, 1 is a water feed pipe, 2 is a propylene feed pipe, 3 is a recycled propylene circulation pipe, 4 is a recycled water circulation pipe, 5 is a reactor, 6 is a cooling condenser, 7 is a gaseous phase discharge pipe, 8 is a liquid phase discharge pipe, 9 is a heat exchanger, 10 is an extraction tower, 11 is a saturated hydrocarbon feed pipe, 12 is an extract phase discharge pipe, 13 and 14 are pressure control valves, 15 is a gas-liquid separator, 16 is a gaseous saturated hydrocarbon discharge pipe, 17 is a crude isopropyl alcohol aqueous solution discharge pipe, 18 is a distillation tower, 19 is a condenser, and 20 is a bottoms discharge pipe.

In FIG. 2, the same reference numbers indicate the same items as in FIG. 1 except for a heat exchanger 21, a liquid-liquid separator 22, and a liquid saturated hydrocarbon discharge pipe 23.

DETAILED DESCRIPTION OF THE PREFERRED EMBODIMENTS

Figure 1:
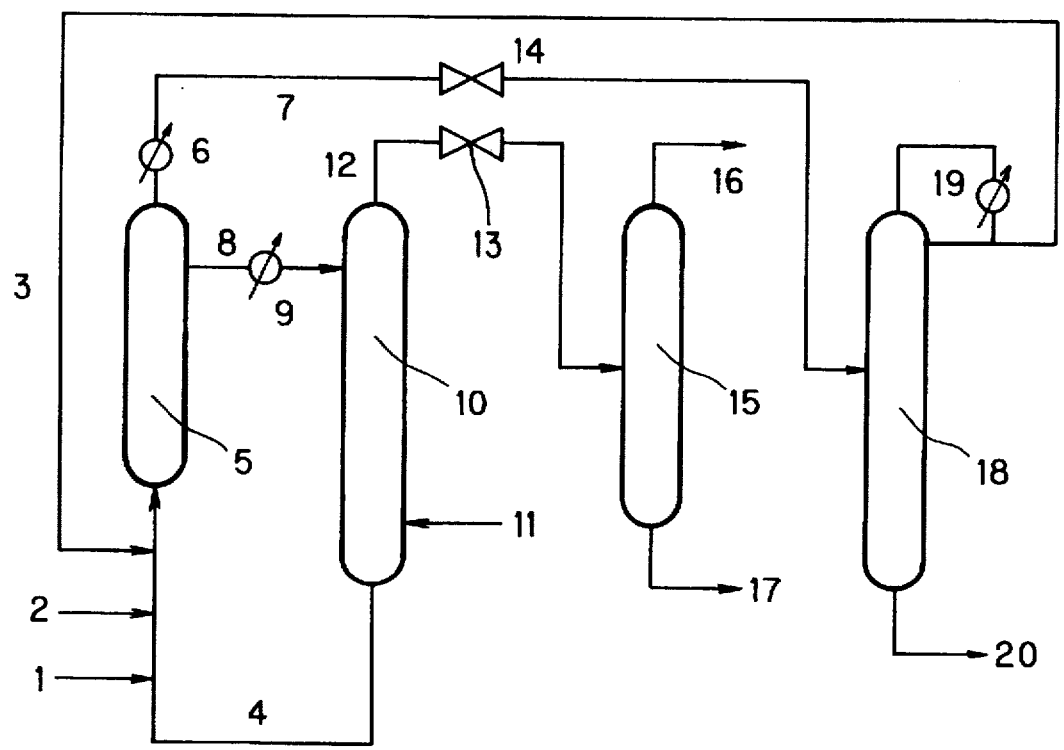
FIG. 1 is a flow sheet embodying the present invention.
Figure 2:
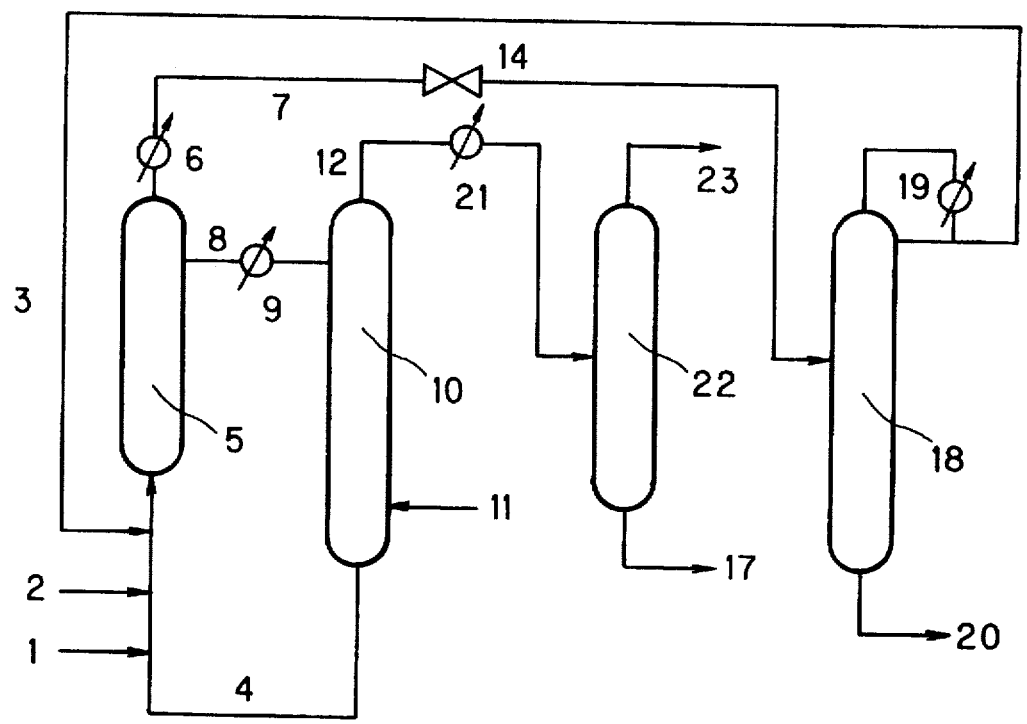
FIG. 2 is another flow sheet embodying the present invention.

A strong acid solid catalyst used in the present invention is not specifically limited and may be a catalyst having a strong acid functional group, especially a strong acid cation exchange resin as a typical example. The solid catalyst may be packed in a reactor as a fixed layer, or may be used therein in the suspending condition. A water-soluble catalyst such as liquid phase heteropolyacid may be used. However, since such a catalyst often requires an expensive acid-resistant material for the reactor and its accessory equipment such as Hastelloy and titanium because of the corrosive property of the catalyst, the solid catalyst is more preferable to be used in the production facilities. The solid catalyst is packed or suspended in the reactor. The reactor used generally is tube type reactor, but is not limited to this type.

In the production process of the present invention, since purification is performed after the total amount of the gaseous phase and the liquid phase of a reacted mixture is continuously drawn out of the reactor and isopropyl alcohol produced by the reaction is extracted from the liquid phase, the reaction is preferably carried out in the conditions in which both of the conversion of propylene from an inlet to an outlet of the reactor and the selectivity of isopropyl alcohol become high.

As mentioned above, when the liquid phase direct hydration of lower olefin such as propylene is carried out in the presence of a strong acid solid catalyst, it is known that the conversion of the raw material olefin reaches 75% or higher and the selectivity of alcohol becomes approximately 95–99%, which are preferable reaction results, by putting the low olefin and water in an amount of at least ten times as much as the stoichiometric amount into coexistence, and by carrying out the reaction at a temperature and a pressure higher than the critical value of the raw material olefin to be used or at a temperature and a pressure slightly lower than the critical value thereof (see, Japanese Patent Publication No. SHO 45-33165).

According to the findings of the inventors of the present invention, when the solid catalyst is used, the reaction is preferably carried out at a temperature of at least between 100° and 250° C. in order to ensure the practical reaction rate. The upper limit of the reaction temperature is mainly determined according to the thermal resistance temperature of the catalyst. For example, when a strong acid solid catalyst having zeolite, silica alumina and others as a base material is employed, the reaction may be carried out at about 250° C. When a strong acid ion exchange resin having a lower thermal resistance temperature is used as the catalyst, the reaction is preferably carried out at 150° C. or lower. On the other hand, a quite high pressure (reaction pressure) is required to dissolve the raw material propylene into the liquid phase where the hydration is carried out. Such a pressure differs depending on the concentration of isopropyl alcohol in the liquid phase which greatly influences the solubility of propylene. According to the findings of the inventors of the present invention, it is practical that the reaction is carried out under at least 60 atm or higher. The upper limit of the pressure is not especially limited, but it is preferably 200 atm or lower in view of the construction of the reactor.

Each of the gaseous phase and the liquid phase of the reacted mixture is continuously drawn out of the reactor. A more preferable example of the present invention may be given by collecting isopropyl alcohol existing in the gaseous phase of the reacted mixture after liquefying the isopropyl alcohol in a cooling condenser mounted at the outlet of the gaseous phase, and also by drawing out substantially the total amount of synthesized isopropyl alcohol from the liquid phase of the reacted mixture. The gaseous phase drawn out of the reactor is continuously fed to a distillation tower, and the unreacted propylene is collected from the top of the distillation tower to recycle into the inlet of the reactor. The raw material propylene used industrially generally contains 4–6% of propane. The propane and a little amount of isopropyl alcohol and water existing in the gaseous phase of the reacted mixture are separated from the bottom of the distillation tower.

The isopropyl alcohol contained in the liquid phase of the reacted mixture continuously drawn out of the reactor may be selectively extracted by contacting the liquid phase with an adequate extraction agent which is in the state of super-critical fluid, sub-critical fluid or liquid, as described above with the respect to the prior art processes. However, as mentioned above, the extraction agent used in such extraction processes exists in the state of gas in general at an ambient temperature under the atmospheric pressure, so that a large compressing power is required for recycling the extraction agent, and it is difficult to collect the extraction agent after the extraction. Furthermore, the facilities necessary for the processes become large-scale since all of the extraction tower and its accessory equipment should be high pressure facilities. Therefore, in using practically such extraction process, it is required to considerably reduce the S/F ratio in the extraction, that is, the amount of the extraction agent to be recycled, rather than to extract alcohol concentrated as highly as possible. However, such requirements cannot be fully satisfied by the processes of the prior art.

In order to solve this problem, the inventors of the present invention have made a comprehensive calculation of the energy required in the process of producing isopropyl alcohol, and have found the process of the present invention can solve the above problems. In the process, the extraction may be carried out at the S/F ratio of 0.3–3, preferably 0.5–2, and more preferably 1–1.5, and also the concentration of the crude isopropyl alcohol aqueous solution collected from the extract phase may be that of the azeotropic composition (88% by weight) or higher. Therefore, the large power required for compressing and recycling the extraction agent and the large-size of the extraction facilities, which have been the substantial problems of the conventional processes, may be greatly reduced, even if an azeotropic distillation using benzene and others is employed as currently practiced in the industrial field to dehydrate the isopropyl alcohol. In the process of the present invention, smaller energy consumption is thus required than in the conventional processes.

As mentioned above, the extraction condition in the present invention may be selected from the conditions in which the extraction agent used becomes super-critical fluid, sub-critical fluid, or liquid. The process in which alcohol is separated from the extract phase which is finally in liquid state, that is, the process described in Japanese Patent Publication Nos. HEI 3-29393 and 5-36419, in which the alcohol is collected from the extract phase drawn out as liquid, or the process of Japanese Patent Publication No. 5-36418, in which the extract phase drawn out as the super-critical fluid or the sub-critical fluid is liquefied by cooling and is subjected to liquid-liquid separation to collect alcohol from the resultant light liquid phase, provides highly concentrated crude alcohol which is almost anhydrous. However, since only a small amount of alcohol can be dissolved in the liquefied extraction agent, the amount of the extraction agent to be recycled becomes inevitably large, and the preferable S/F ratio mentioned above cannot be attained.

In order to attain the above-mentioned low S/F ratio, it is essential to collect the isopropyl alcohol from the extract phase in the super-critical or sub-critical fluid in which a larger amount of the isopropyl alcohol can be dissolved than in the liquid condition of the extraction agent. Even when the collected crude isopropyl alcohol does not become anhydrous in consequence, the process of the present invention is much more advantageous in view of the total energy necessary for the production process if the alcohol is at the concentration of the azeotropic composition or a higher concentration.

Unsaturated hydrocarbons such as propylene or $CO_2$ have been proposed for use as an extraction agent for concentrating alcohols. However, the inventors of the present invention have made a surprising finding which hasn't been expected by those skilled in the art. According to this finding, the extracted amount of isopropyl alcohol is larger (i.e. the concentration in the extract phase is higher) in comparison of the extraction property of the extraction agent for the same extraction feed (i.e. low-concentration isopropyl alcohol) when using as the extraction agent a saturated hydrocarbon having 3 or 4 carbon atoms, more specifically, any one of propane, i-butane and n-butane, or the mixture thereof, rather than using the unsaturated hydrocarbons. Furthermore, when using the saturated hydrocarbon, isopropyl alcohol is more selectively extracted than water, and only a small amount of the extraction agent is dissolved into the raffinate phase mainly consisting of water or into the solute separated from the extract phase (high-concentrated isopropyl alcohol aqueous solution). Thus, the extraction can be practiced more effectively and more advantageously in view of the necessary energy as mentioned above. The process of the present invention is effectuated based on this finding.

For example, according to the experimental examination of the inventors of the present invention, comparing the gas-liquid equilibrium of the three components of water, isopropyl alcohol and the extraction agent (any one of propane, propylene and $CO_2$) at a temperature in a range between 120° and 130° C. and a pressure in a range between 80 and 100 atm, the concentration of the isopropyl alcohol in the gaseous phase in equilibrium with the liquid phase obtained by using propane as the extraction agent is unexpectedly 1.2–2.5 times higher than that obtained by using propylene and $CO_2$ as the extraction agent, when the concentration of the isopropyl alcohol in the liquid phase free of the extraction agent is 15–20% by weight. Furthermore, when the concentration of the isopropyl alcohol in the gaseous phase is converted into the concentration of the alcohol free of the extraction agent, the converted concentration obtained by using propane as the extraction agent is as high as over 90% by weight while the concentration obtained by using propylene or $CO_2$ as the extraction agent is about 75–85% by weight. On the other hand, comparing the concentration of the extraction agent dissolved in the liquid phase, it is about 0.1–1 mol % when the extraction agent is propane, which is about from ½ to 1/10 of the concentration obtained when the extraction agent is propylene or $CO_2$.

When the gas-liquid equilibrium of the four components of propylene, propane, isopropyl alcohol, and water under a high pressure is precisely measured, it has been found that the solubility of propylene into the liquid phase mainly consisting of isopropyl alcohol and water becomes extremely low due to the coexistence of propane. This result means that, in extracting the isopropyl alcohol as being the reaction product from the liquid phase continuously drawn out from the reactor, the isopropyl alcohol can be much more effectively extracted by using a saturated hydrocarbon such as propane as the extraction agent than using propylene as the extraction agent as in the conventional process, and also means that the unreacted propylene dissolved in the liquid phase can be collected simultaneously. Thus, this result shows that the production process of the present invention is effective for the improvement of the propylene unit.

For the practical use of the process of the present invention, it is preferable that the major amount of the collected saturated hydrocarbon is recycled to be used as the extraction agent after the crude isopropyl alcohol aqueous solution is separated from the extract phase mainly consisting of the saturated hydrocarbon. A preferable embodiment of the production process of the present invention is that the unreacted propylene collected from the liquid phase of the reacted mixture during the extraction operation may be collected by means of distillation by feeding a part of the saturated hydrocarbon to the distillation tower together with the gaseous phase of the reacted mixture.

As mentioned above, in order to carry out the extraction in the conditions in which the extraction agent becomes super-critical fluid or sub-critical fluid, it is required, needless to say, that the extraction is practiced at a temperature equal to or higher than the critical temperature of the saturated hydrocarbon having 3 or 4 carbon atoms used as the extraction agent under a pressure equal to, higher than, or slightly lower than the critical pressure of the saturated hydrocarbon.

It is known that the extraction temperature gives a great effect on the extracted amount (i.e. the concentration in the extract phase) and the extraction selectivity (i.e. the concentration free of hydrocarbon in the extract phase) of the isopropyl alcohol. The lower the extraction temperature is, the more selectively the alcohol can be extracted, while the extracted amount of the isopropyl alcohol, that is, the concentration in the extract phase becomes lower. Thus, it is necessary to select a preferable extraction temperature from a viewpoint of chemical engineering considering this relationship. According to the finding of the inventors of the present invention, when the extraction is carried out by using the saturated hydrocarbon having 3 or 4 carbon atoms as the extraction agent under an adequate extraction pressure, it is preferable to practice the extraction at a temperature in a range between the critical temperature of the extraction agent (the critical temperature of the mixture when the extraction agent is a mixture of the saturated hydrocarbons having 3 and 4 carbon atoms) and the temperature higher than the critical temperature by 40° C. in order to extract the isopropyl alcohol, which is synthesized under the above conditions and contained in the reacted mixture at about 15-27% by weight, at the concentration of the azeotropic composition of 88% by weight free of the hydrocarbons or higher. The extract phase is liquefied at a temperature lower out of this temperature range. When the temperature is higher out of the temperature range, the concentration of isopropyl alcohol free of the hydrocarbons in the extract phase does not reach the azeotropic concentration.

The extraction pressure greatly influences both of the extracted amount and the extraction selectivity of isopropyl alcohol. This is mainly because the pressure is a direct factor which determines the density of the extraction agent of the saturated hydrocarbon. In order for the saturated hydrocarbon to have excellent properties as the extraction agent, it is required that the extraction agent has a high density, more specifically, that the extraction agent becomes super-critical fluid. In general, the density of the super-critical fluid becomes higher as the pressure becomes higher. When the extraction agent is a mixture, the fluid density greatly differs depending on its composition. The inventors of the present invention have found that, in the case of the super-critical fluid consisting of a saturated hydrocarbon having 3 or 4 carbon atoms, isopropyl alcohol, and water like the extract phase obtained in the process of the present invention, the density of the fluid does not substantially change even when the extraction pressure is higher than 200 atm. Therefore, the extraction pressure is preferably in a range between the critical pressure of the hydrocarbon used as the extraction agent and 200 atm.

An example in which propane is mainly used as the saturated hydrocarbon is now described.

It is preferable that the extraction is carried out in a countercurrent multi-stage contact type extractor as in the process of a liquid-liquid extraction in order to effectively reduce the S/F ratio, that is, the amount of the extraction agent to be recycled. For example, as shown in Example 1 described below, a desirable result of the extraction of isopropyl alcohol is obtained at the S/F ratio of around 1 by employing propane as the extraction agent and countercurrently contacting the extraction agent with the liquid phase of the reacted mixture under the preferable extraction conditions.

The S/F ratio may be smaller than 1. However, when the S/F ratio is too small, the concentration of the isopropyl alcohol remaining in the raffinate phase becomes high to give unfavorable effects on the reaction. Therefore, the S/F ratio may be at least 0.3 or larger, preferably 0.5 or larger, and more preferably 1 or larger. Further, the ratio should be set to be 3 or smaller in order to save the energy for concentrating isopropyl alcohol more than in the process of distillation, and further the ratio is preferably 2 or smaller, and more preferably 1.5 or smaller since the facilities are operated under a high pressure.

Since water is the main component of the raffinate phase remaining after the isopropyl alcohol is extracted from the liquid phase of the reacted mixture, it is desirable, needless to say, that the major amount of the raffinate phase is recycled into the reactor. It is preferable that the amount of the raffinate phase to be recycled into the reactor is established such that the total amount of newly charged water and the recycled water to be fed into the inlet of the reactor is at least 10 times or more in mole as much as the feed amount of propylene to be reacted as known in the art in order to enhance the selectivity of isopropyl alcohol in the reaction.

For separating the isopropyl alcohol of the reaction product as the highly concentrated aqueous solution from the extract phase in the super-critical or sub-critical state which is obtained by contacting the liquid phase of the reacted mixture and the extraction agent and which mainly consists of the saturated hydrocarbon, either of the two following processes may be selected: a process for separating into the gaseous phase mainly consisting of the saturated hydrocarbon and the liquid phase mainly consisting of isopropyl alcohol and water by reducing the pressure of the extract phase to the critical pressure of the extraction agent or a lower pressure; and a process for separating into the light liquid phase mainly consisting of saturated hydrocarbon and the heavy liquid phase mainly consisting of isopropyl alcohol and water by cooling the extract phase to the temperature of the critical temperature of the extraction agent or a lower temperature while substantially maintaining the pressure.

First, the process for separating the crude isopropyl alcohol aqueous solution by reducing the pressure of the extract phase is described. In general, the lower the pressure of the extract phase is reduced, the lower the density thereof becomes. Thus, since the extraction capacity of the extraction agent is lowered under a lower pressure, the extracted isopropyl alcohol and water condense to be more completely separated from the extraction agent. However, needless to say, a larger power is required for compressing the extraction agent to be recycled. According to the examination of the inventors of the present invention, the pressure of the extract phase is reduced to be in a range between 5 atm and the critical pressure of the extraction agent, and more preferably in a range between 10 atm and the pressure lower than the critical pressure by 5 atm, considering the balance between the separateness of the extraction agent and the crude isopropyl aqueous alcohol solution and the power for re-compressing and recycling the extraction agent.

This separation process itself is known in the art. However, only a small amount of the extraction agent is dissolved into the isopropyl alcohol aqueous solution when using the saturated hydrocarbon having 3 or 4 carbon atoms as the extraction agent as mentioned above. For this reason, the extraction agent dissolved in the crude isopropyl alcohol aqueous solution separated from the extract phase is not necessarily required to be collected for practical use. In the production process of the present invention, propane contained in propylene used industrially is generally separated from the bottom of the distillation tower when collecting the unreacted propylene by distillation. If the propane is used as the saturated hydrocarbon of the extraction agent, the amount of the newly charged extraction agent is reduced, or the extraction agent is not required to be newly charged, which results in a preferable embodiment of the present invention. Further, only a small amount of the evaporated isopropyl alcohol is contained in the gaseous phase of the reacted mixture continuously drawn out of the reactor, and such isopropyl alcohol is obtained from the bottom of the distillation tower together with propane when collecting the unreacted propylene from the gaseous phase by distillation. The isopropyl alcohol is collected without fail by using the propane as the extraction agent, which is advantageous in view of the raw material unit.

Next, the process for separating the crude isopropyl alcohol aqueous solution by liquefying the extract phase by means of cooling is described. In this process, it is required to cool the extract phase at least to the critical temperature of the extraction agent or lower while substantially maintaining the pressure in order to liquefy the major amount of the extract phase. For liquefying substantially the total amount of the extract phase, the temperature is preferably 10° C. lower than the critical temperature or lower, and more preferably 20° C. lower than the critical temperature or lower. It is not preferable to cool the extract phase to an excessively low temperature since it causes a loss of energy.

This process itself is also well known in the art. However, the process of the present invention is explicitly different from the process of the above-mentioned Japanese Patent Publication No. HEI 5-36418 in that the isopropyl alcohol is collected from the heavy liquid phase mainly consisting of isopropyl alcohol and water separated by liquefying the extract phase, while the alcohol is collected from the light liquid phase in the process of the above patent. As mentioned above, the solubility of the isopropyl alcohol and water into liquefied saturated hydrocarbon is extremely low, so that the extract phase is separated into the light liquid phase consisting of almost only the saturated hydrocarbon and the heavy liquid phase mainly consisting of isopropyl alcohol and water by cooling the extract phase. By collecting the crude isopropyl alcohol as the heavy liquid phase, it becomes just advantageous that the extraction is carried out under the super-critical or sub-critical state of the extraction agent, and the intended S/F ratio of 0.3–3, preferably 0.5–2, and more preferably 1–1.5 is attained. Furthermore, since the amount of the extraction agent dissolved in the heavy liquid phase is also small, a preferable embodiment can be given by using the propane contained in the raw material propylene as the saturated hydrocarbon of the extraction agent.

When the isopropyl alcohol aqueous solution is separate from the extracted phase by reducing the pressure thereof, the extraction agent is required to be re-compressed to the extraction pressure in recycling the collected extraction agent. On the other hand, when the solution is separated from the extract phase liquefied by cooling, the pressure is kept high. Thus, at least in view of the power required for re-compressing and recycling the extraction agent, the latter process is advantageous.

As mentioned above, according to the production process of the present invention, a high conversion of propylene and a high selectivity of isopropyl alcohol are attained by carrying out the liquid phase direct hydration at a temperature and a pressure preferable for the reaction. Furthermore, the crude isopropyl alcohol can be collected easily and effectively at the concentration equal to or higher than the concentration of the azeotropic composition by subjecting the liquid phase of the reacted mixture containing the major amount of the synthesized isopropyl alcohol to extraction at a preferable temperature and a preferable pressure using the saturated hydrocarbon having 3 or 4 carbon atoms as the extraction agent, and then by reducing the pressure of the extract phase or cooling the extract phase. Thus, the large energy required for the concentration of isopropyl alcohol in a conventional production process can be reduced. Moreover, as a result large-scale facilities are not required for the reaction and the extraction, so that the production process of the present invention is preferable for practical use. The dehydration and concentration of the crude isopropyl alcohol aqueous solution obtained at a concentration equal to or higher than the azeotropic composition can be easily practiced by a known dehydration process by means of azeotropic distillation using a solvent such as benzene, toluene and hexane which forms an azeotropic mixture with water as generally practiced industrially.

Therefore, the process of the present invention as a novel process for producing isopropyl alcohol is highly applicable in the industrial field.

EXAMPLES

Examples of the present invention are now described.

Example 1

In a jacketed reactor manufactured by SUS 316 having the inner diameter of 30 mm and the height of 300 mm, 100 ml of commercially available macro-porous type strong acid cation exchange resin, Levachitt SPC-118, was filled. From the bottom of the reactor, 96% of propylene (the remaining 4% was propane) at the flow rate of 230 mmol (9.6 g) per hour, pure water at the flow rate of 5.5 g per hour, and recycled water (the raffinate liquid) at the flow rate of 67 g per hour were fed. The temperature and the pressure of the reactor were kept at 150° C. and 80 atm. respectively. A gaseous phase continuously discharged from the top of the reactor was fed to a distillation tower manufactured by SUS 316 having the inner diameter of 20 mm and 50 plates and a feed plate at the fifteenth plate from the top of the tower after the pressure of the gaseous phase was reduced to 30 atm by a pressure control valve, and the gaseous phase was continuously distilled at reflux ratio of 13. Liquid containing propane as the main component was separated from the bottom of the distillation tower. Unreacted propylene having almost the same purity as that of the raw material was drawn out from the top of the distillation tower. The total amount of the unreacted propylene was continuously recycled to the reactor. On the other hand, a liquid phase continuously drawn out from the upper portion of the reactor at the rate of 81 g per hour was cooled to 130° C., and then was fed to the upper portion of a jacketed countercurrent extractor manufactured by SUS 316 having the inner diameter of 50 mm and the height of 8 m. Propane as an extraction agent was continuously fed in the amount of 94 g per hour to the lower portion of the extractor. The extraction was carried out at 130° C. under 80 atm. The total amount of raffinate liquid continuously drawn out at the rate of 67 g per hour from the bottom of the extractor was recycled into the reactor. An extract phase continuously drawn out at the rate of 108 g per hour from the top of the extractor was partly liquefied by controlling the temperature at 80° C. in a gas-liquid separator after the pressure of the extract phase was reduced to 30 atm by a pressure control valve. Then, the liquefied phase and remaining gas were continuously drawn out from the gas-liquid separator. At the time when all reached the steady state, the liquefied phase was continuously drawn out at the rate of about 14.3 g per hour from the gas-liquid separator. When the composition of the liquefied phase was examined, it contained about 89% by weight of isopropyl alcohol, about 10% by weight of water, and about 1% by weight of di-isopropyl ether.

Example 2

Example 1 was repeated except that the extract phase continuously drawn out at the rate of 108 g per hour from the top of the extractor was cooled to 60° C. to be liquefied while keeping the pressure, that the liquefied extract phase was introduced into a liquid-liquid separator to separate into light and heavy liquid phases, and that the light liquid phase and the heavy liquid phase were continuously drawn out from the liquid-liquid separator. At the time when all reached the steady state, the heavy liquid phase was continuously drawn out at the rate of about 14.4 g per hour from the separator. When the composition of the heavy liquid phase was examined, it contained about 88% by weight of isopropyl alcohol, about 11% by weight of water, and about 1% by weight of di-isopropyl ether.

Comparative Example 1

Example 1 was repeated except that the steps after the extraction were not carried out, and that the pure water was fed to the reactor at the rate of about 72.5 g per hour and the liquid phase of the reacted mixture was continuously drawn out at the rate of about 81 g per hour from the reactor. The liquid phase contained about 18% by weight of isopropyl alcohol, and about 82% by weight of water.

Comparative Example 2

Example 1 was repeated except that the extraction was carried out at 150° C. The liquefied phase was continuously drawn out at the rate of about 16 g per hour from the gas-liquid separator. The liquefied phase contained about 80% by weight of isopropyl alcohol, about 19% by weight of water, and about 1% by weight of di-isopropyl ether.

The crude isopropyl alcohol was not concentrated to the concentration of the azeotropic composition since the isopropyl alcohol was not selectively extracted because of the high extraction temperature.

Comparative Example 3

Example 1 was repeated except that propylene was used as the extraction agent instead of propane. When the composition of the liquefied phase was examined which was continuously drawn out from the gas-liquid separator at the rate of about 15 g per hour, the liquefied phase contained about 83% by weight of isopropyl alcohol, about 16% by weight of water, and about 1% by weight of di-isopropyl ether.

The crude isopropyl alcohol was not concentrated to the concentration of the azeotropic composition since the isopropyl alcohol was extracted less selectively by using the extraction agent of propylene as compared with the case where the extraction agent of propane is used.

What is claimed is:

1. A process for producing isopropyl alcohol which comprises direct hydration of propylene and water at a high temperature and a high pressure in the presence of a strong acid solid catalyst, separation of crude isopropyl alcohol aqueous solution from the resultant reacted mixture and purification of said solution, characterized in that the process comprises the steps of:

(1) feeding continuously propylene and water, said water being in the amount of at least 1 mole per 1 mole of propylene to be reacted into a reactor in which a solid catalyst is packed or suspended to react them at a temperature ranging between 100° and 250° C. and a pressure in a range between 60 and 200 atm;

(2) drawing out continuously the total amount of a gaseous phase and a liquid phase of the reacted mixture from the reactor;

(3) feeding the gaseous phase of said reacted mixture to a distillation tower to remove impurities consisting essentially of propane contained in the raw material propylene from the bottom of the tower and to collect unreacted propylene from the top of the tower s as to recycle the unreacted propylene into an inlet of the reactor;

(4) contacting the liquid phase of said reacted mixture with an extraction agent of a saturated hydrocarbon having 3 or 4 carbon atoms at a temperature ranging between the critical temperature of said extraction agent and the temperature higher than the critical temperature by 40° C. under a pressure ranging between the critical pressure of said extraction agent and 200 atm. at an S/F ratio ranging between 0.3 to 3 which is calculated from the equation of the amount of said extraction agent divided by the amount of the extraction feed, and extracting isopropyl alcohol as a reaction product from the liquid phase of said reacted mixture;

(5) recycling to the reactor the major amount of the raffinate liquid obtained by extracting isopropyl alcohol from the liquid phase of said reacted mixture, the raffinate liquid consisting essentially of water; and (6) separating the isopropyl alcohol as a highly concentrated aqueous solution from the extract phase consisting essentially of said saturated hydrocarbon, and purifying said solution to obtain purified isopropyl alcohol.

2. A process for producing isopropyl alcohol a claimed in claim 1, wherein the process comprises the step of separating the extract phase into the gaseous phase consisting essentially of said saturated hydrocarbon and the liquid phase consisting essentially of isopropyl alcohol and water by reducing the pressure of the extract phase to the critical pressure of said saturated hydrocarbon or lower to obtain the isopropyl alcohol produced by the reaction as the highly concentrated aqueous solution from the extract phase wherein the extract phase is obtained by contacting the liquid phase of said reacted mixture and said extraction agent and consists essentially of said saturated hydrocarbon.

3. A process for producing isopropyl alcohol as claimed in claim 1, wherein the process comprises the step of separating the extract phase into a light liquid phase consisting essentially of said saturated hydrocarbon and a heavy liquid phase consisting essentially of isopropyl alcohol and water by cooling the extract phase to the critical temperature of said saturated hydrocarbon or lower while substantially maintaining the pressure of the extract phase to obtain the isopropyl alcohol produced by the reaction as highly concentrated aqueous solution from the extract phase wherein the extract phase is obtained by contacting the liquid phase of said reacted mixture and said extraction agent and consists essentially of said saturated hydrocarbon.

4. A process for producing isopropyl alcohol as claimed in claim 3, wherein the process comprises the step of recycling as the extraction agent the major amount of said saturated hydrocarbon collected after separating the isopropyl alcohol produced by the reaction as the highly concentrated aqueous solution from the extract phase consisting essentially of said saturated hydrocarbon obtained by contacting the liquid phase of said reacted mixture and said extraction agent.

5. A process for producing isopropyl alcohol as claimed in claim 4, comprising the steps of drawing out a part of said saturated hydrocarbon to be recycled as said extraction agent, feeding said saturated hydrocarbon to the distillation tower together with the gaseous phase of said reacted mixture, and separating said saturated hydrocarbon from the bottom of the distillation tower.

6. A process for producing isopropyl alcohol as claimed in claim 5, wherein said saturated hydrocarbon is propane.

7. A process for producing isopropyl alcohol as claimed in claim 6, wherein at least a part of propane for said extraction agent is the propane that is contained in the raw material propylene and is separated from the bottom of the distillation tower for collecting the unreacted propylene.

8. A process for producing isopropyl alcohol as claimed in claim 2, wherein the process comprises the step of recycling as the extraction agent the major amount of said saturated hydrocarbon collected after separating the isopropyl alcohol produced by the reaction as the highly concentrated aqueous solution from the extract phase mainly consisting of said saturated hydrocarbon obtained by contacting the liquid phase of said reacted mixture and said extraction agent.

9. A process for producing isopropyl alcohol as claimed in claim 8, comprising the steps of drawing out a part of said saturated hydrocarbon to be recycled as said extraction agent, feeding said saturated hydrocarbon to the distillation tower together with the gaseous phase of said reacted mixture, and separating said saturated hydrocarbon from the bottom of the distillation tower.

10. A process for producing isopropyl alcohol as claimed in claim 9, wherein said saturated hydrocarbon is propane.

11. A process for producing isopropyl alcohol as claimed in claim 10, wherein at least a part of propane for said extraction agent is the propane that is contained in the raw material propylene and is separated from the bottom of the distillation tower for collecting the unreacted propylene.

12. A process for producing isopropyl alcohol as claimed in claim 1, wherein the process comprises the step of recycling as the extraction agent the major amount of said saturated hydrocarbon collected after separating the isopropyl alcohol produced by the reaction as the highly concentrated aqueous solution from the extract phase mainly consisting of said saturated hydrocarbon obtained by contacting the liquid phase of said reacted mixture and said extraction agent.

13. A process for producing isopropyl alcohol as claimed in claim 12, comprising the steps of drawing out a part of said saturated hydrocarbon to be recycled as said extraction agent, feeding said saturated hydrocarbon to the distillation tower together with the gaseous phase of said reacted mixture, and separating said saturated hydrocarbon from the bottom of the distillation tower.

14. A process for producing isopropyl alcohol as claimed in claim 13, wherein said saturated hydrocarbon is propane.

15. A process for producing isopropyl alcohol as claimed in claim 14, wherein at least a part of propane for said extraction agent is the propane that is contained in the raw material propylene and is separated from the bottom of the distillation tower for collecting the unreacted propylene.

16. A process for producing isopropyl alcohol as claimed in claim 4, wherein said saturated hydrocarbon is propane.

17. A process for producing isopropyl alcohol as claimed in claim 8, wherein said saturated hydrocarbon is propane.

18. A process for producing isopropyl alcohol as claimed in claim 12, wherein said saturated hydrocarbon is propane.

19. A process for producing isopropyl alcohol as claimed in claim 3, wherein said saturated hydrocarbon is propane.

20. A process for producing isopropyl alcohol as claimed in claim 2, wherein said saturated hydrocarbon is propane.

21. A process for producing isopropyl alcohol as claimed in claim 1, wherein said saturated hydrocarbon is propane.

22. A process for producing isopropyl alcohol as claimed in claim 16, wherein at least a part of propane for said extraction agent is the propane that is contained in the raw material propylene and is separated from the bottom of the distillation tower for collecting the unreacted propylene.

23. A process for producing isopropyl alcohol as claimed in claim 20, wherein at least a part of propane for said extraction agent is the propane that is contained in the raw material propylene and is separated from the bottom of the distillation tower for collecting the unreacted propylene.

24. A process for producing isopropyl alcohol as claimed in claim 21, wherein at least a part of propane for said extraction agent is the propane that is contained in the raw material propylene and is separated from the bottom of the distillation tower for collecting the unreacted propylene.

25. A process for producing isopropyl alcohol as claimed in claim 1, wherein the S/F ratio is between 0.5 and 2.

26. A process for producing isopropyl alcohol as claimed in claim 1, wherein the S/F ratio is between 1 and 1.5.

* * * * *

UNITED STATES PATENT AND TRADEMARK OFFICE
CERTIFICATE OF CORRECTION

PATENT NO. : 5,763,693
DATED : June 9, 1998
INVENTOR(S) : Shigeru HIRATA et al

It is certified that error appears in the above-identified patent and that said Letters Patent is hereby corrected as shown below:

ON THE TITLE PAGE:

Insert the following:

-- [30] Foreign Application Priority Data

February 24, 1995 [JP] Japan.................7-37136 --.

In claim 1, column 16, line 45, after "tower" delete "s".

In claim 2, column 17, line 3, after "alcohol" delete "a" and insert --as--.

Signed and Sealed this

Twentieth Day of April, 1999

Attest:

Q. TODD DICKINSON

*Attesting Officer*   Acting Commissioner of Patents and Trademarks